US00PP13046P2

(12) United States Plant Patent
Noodelijk

(10) Patent No.: US PP13,046 P2
(45) Date of Patent: Oct. 1, 2002

(54) CHRYSANTHEMUM PLANT NAMED 'AMOR'

(75) Inventor: Robert Noodelijk, Woubrugge (NL)

(73) Assignee: Chrysanthemum Breeders Association NV (NL)

( * ) Notice: Subject to any disclaimer, the term of this patent is extended or adjusted under 35 U.S.C. 154(b) by 0 days.

(21) Appl. No.: 09/734,607

(22) Filed: Dec. 13, 2000

(51) Int. Cl.[7] ..... A01H 5/00
(52) U.S. Cl. ..... Plt./292
(58) Field of Search ..... Plt./292

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A chrysanthemum plant named 'AMOR' characterized by its medium sized blooms with pink ray florets and prolific branching; natural season flower date September 4–9; blooming for a period of 7 weeks.

3 Drawing Sheets

BACKGROUND OF THE INVENTION

'Amor' is a product of a breeding and selection program for outdoor pot mums (garden mums) which had the objective of creating new chrysanthemum cultivars with a decorative type flower, a natural season flower date around September 4–9; blooming for a period of 7 weeks. The new plant of the present invention comprises a new and distinct cultivar of Chrysanthemum plant. 'AMOR' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout Holland in September 1997. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
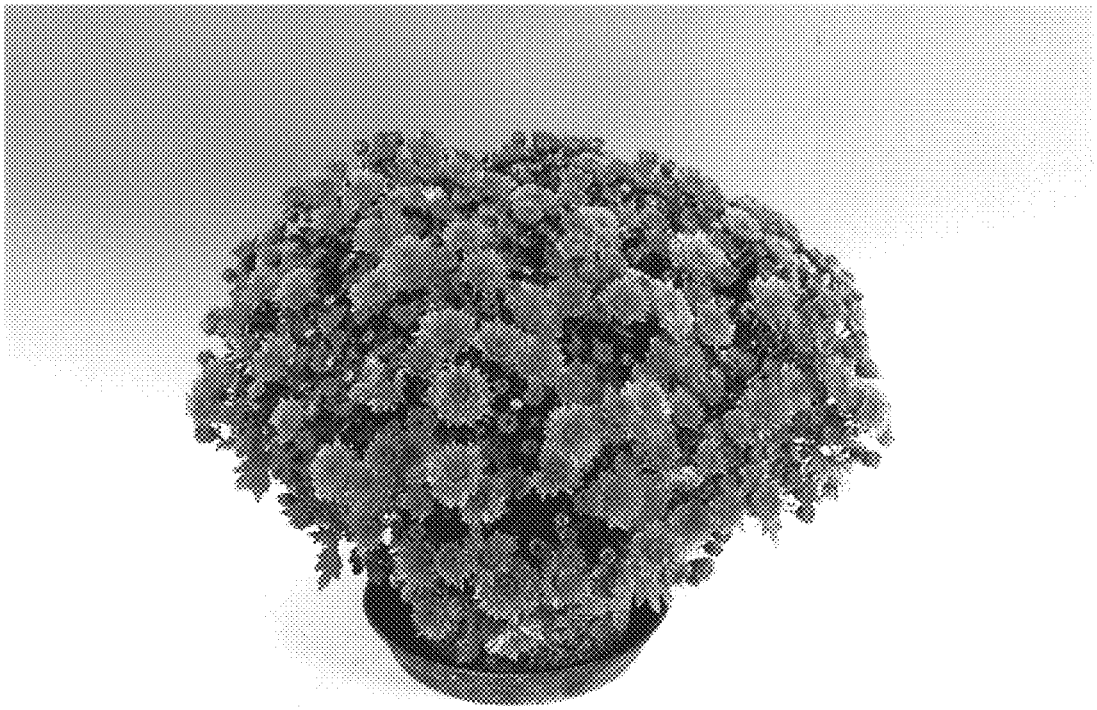
FIG. 1 shows a plant of the cultivar in full bloom.
Figure 2:
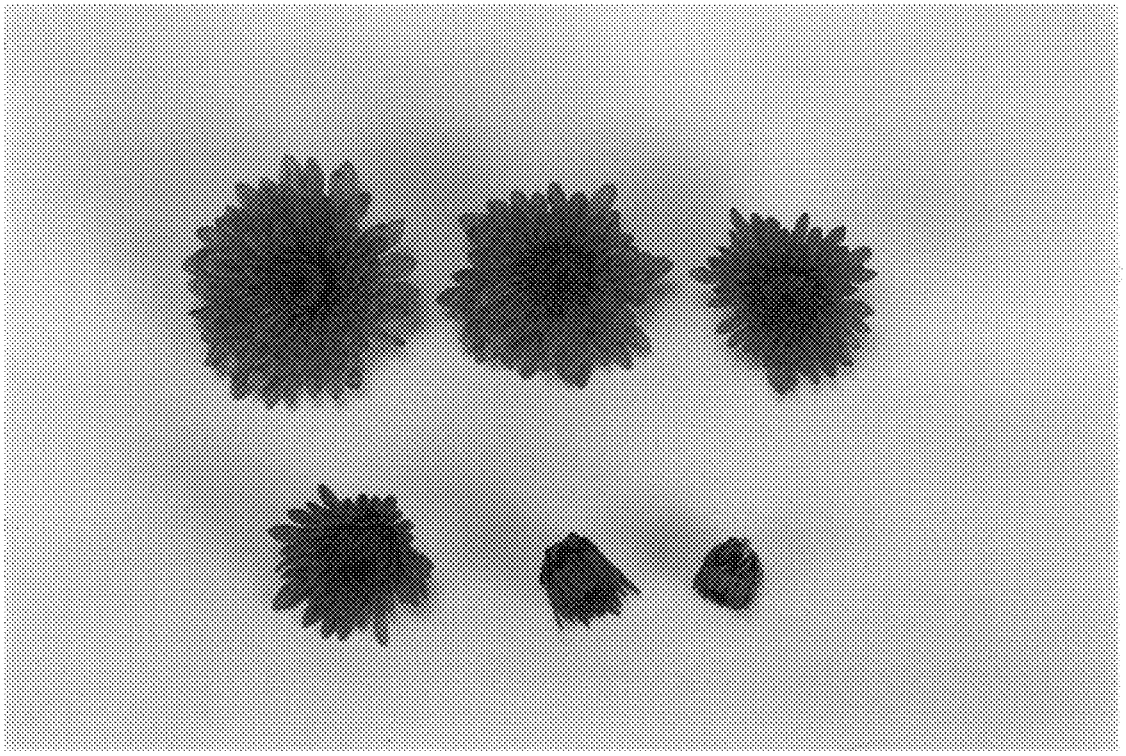
FIG. 2 shows the various stages of bloom of the new cultivar.
Figure 3:
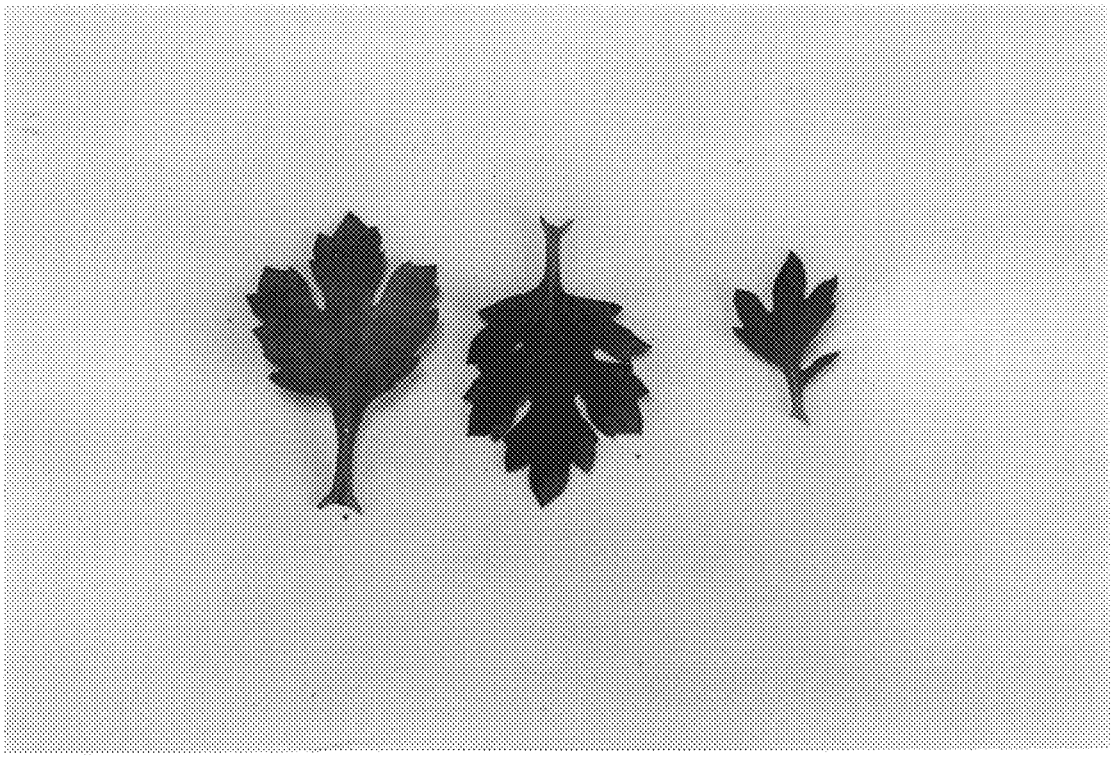
FIG. 3 shows the various stages of foliage and petiole of the new cultivar.

This new variety of chrysanthemum is of the botanical classification *Chrysanthemum morifolium*. The observations and measurements were gathered from plants grown out door in Rijsenhout, Holland under natural day length and temperature and planted week 22 in 1998 and 1999. The natural blooming date of this crop was September 4–9 (week 36). The average height of the plants was 32–36 cms. No growth retardants were used. No tests were done on disease or insects resistance or susceptibility. No tests were done on cold or drought resistance. This new variety produces medium sized blooms with pink ray florets and a pale pink center blooming for a period of 7 weeks.

From the cultivars known to inventor the most similar existing cultivar in comparison to 'AMOR' is 'LYNN' (U.S. Plant Pat. No. 8,171). When 'LYNN' and 'AMOR' are being compared, the following differences are noticed: The differences of 'LYNN' and 'AMOR' are (1) Natural blooming date. 'AMOR' flowers earlier. (2) Branching. 'AMOR' branches more prolific. (3) Plant shape. The plant of 'AMOR' is more mounded.

The following is a description of the plant and characteristics that distinguish 'AMOR' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Table 1: Botanical Description of Cultivar 'Amor'

*Size.*—Medium; cross-section 1.2 cm, height 1.0 cm.
*Outside color.*—Red-purple 74 C.
*Involucral bracts.*—2 rows, length 7 mm, width 3 mm.
*Involucral bracts among disc-florets.*—Not present.
*Involucral bracts color.*—Green 138 B.
*Type.*—Decorative.
*Height.*—High, 3.0–3.5 cm.
*Size.*—Medium.
*Fully expanded.*—5.0–5.5 cm.
*Number of blooms per branch.*—Approx. 5 blooms per branch.
*Performance on the plant.*—7 weeks.
*Seeds (if crossed).*—Produced in small quantities, ovate. Grey-brown 199 A, 1½ mm in length.
*Fragrance.*—Typical chrysanthemum, slight.
*Center of the flower (disc-florets).*—Immature Red-purple 74 B. Mature Red-purple 74 D.
*Color of upper surface of the ray-florets.*—Red-purple 74 C.
*Color of the lower surface of the ray-florets.*—Red-purple 74 D.
*Tonality from distance.*—A mounded decorative garden mum with pink blooms.
*Color of the upper surface of the flowers after aging of the plant.*—To red-purple 74 D.

Ray florets:

*Texture.*—Upper and under side smooth.

*Number.*—200–230.

*Cross-section.*—Concave.

*Longitudinal axis of majority.*—Incurved to straight.

*Length of corolla tube.*—Medium, 0.9–1.1 cm.

*Ray-floret margin.*—Entire.

*Ray-floret length.*—2.5–2.8 cm.

*Ray-floret width.*—0.4–0.6 cm.

*Ratio length/width.*—High.

*Shape of tip.*—Pointed.

*Disc florets.*—Not present.

Reproductive organs:

*Stamen.*—Not present.

*Pollen.*—Not present.

*Styles.*—Thin.

*Style color.*—Yellow-green 144 A.

*Style length.*—4 mm.

*Stigmas color.*—Yellow-green 144 A.

*Stigma width.*—1 mm.

*Ovaries.*—Enclosed in calyx.

Plant:

*Shape.*—Grown as a spray-type pot-mum, outdoor mounded and round.

*Growth habit.*—Spreading.

*Growth rate.*—Moderate.

*Height.*—32–36 cm.

*Width.*—35–40 cm.

*Stem color.*—Green 138 B.

*Stem strength.*—Strong.

*Stem brittleness.*—Present.

*Stem anthocyanin coloration.*—Present, a thin layer of greyed-red 181 A mainly at the base of the stem.

*Length of lateral branch.*—From top to bottom 12–13 cm.

*Lateral branch color.*—Green 138 B.

*Lateral branch, attachment.*—Weak.

*Branching* (*average number of lateral branches*).—Mounding and prolific with 8–10 breaks after pinching.

*Peduncle length.*—4.0–4.5 cm.

*Peduncle color.*—Green 138 B.

*Natural season blooming date.*—September 4–9.

Foliage:

*Color of mature leaves.*—Upper side green 138 A. Under side green 138 B.

*Color of immature leaves.*—Upper side green 138 A. Under side green 138 B.

*Size.*—Small; length 6 cm, width 5 cm.

*Quantity* (*number per lateral branch*).—12–14.

*Shape.*—Oval.

*Texture upper side.*—Glabrous.

*Texture under side.*—Pubescent.

*Venation arrangement.*—Palmate.

*Shape of the margin.*—Serrated.

*Shape of base of sinus between lateral lobes.*—Acute.

*Margin of sinus between lateral lobes.*—Diverging.

*Shape of base.*—Asymmetric.

*Apex.*—Mucronate.

TABLE 2

Difference with the comparison varieties (when grown under the same conditions)

| | 'AMOR' | 'LYNN' |
|---|---|---|
| Natural blooming date | September 4–9 | September 26–29 |
| Branding | Mounded and prolific | Moderate |
| Plant shape | Mounded | Semi-upright |

I claim:

1. A new and distinct variety of chrysanthemum plant as described and illustrated.

* * * * *